United States Patent
Yoshikoshi et al.

[11] Patent Number: 5,176,144
[45] Date of Patent: Jan. 5, 1993

[54] CARDIAC OUTPUT MEASURING CATHETER

[75] Inventors: Akiko Yoshikoshi; Kouji Tsuchida, both of Kanagawa, Japan

[73] Assignee: Terumo Kabushiki Kaisha, Tokyo, Japan

[21] Appl. No.: 825,821

[22] Filed: Jan. 27, 1992

Related U.S. Application Data

[63] Continuation of Ser. No. 581,469, Sep. 11, 1990, abandoned.

[30] Foreign Application Priority Data

Sep. 14, 1989 [JP] Japan .................. 1-238663

[51] Int. Cl.$^5$ ............................................. A61B 5/028
[52] U.S. Cl. ................................ 128/692; 128/713; 128/736
[58] Field of Search ............... 128/691, 692, 693, 713, 128/736

[56] References Cited

U.S. PATENT DOCUMENTS

| | | | |
|---|---|---|---|
| 4,632,125 | 12/1986 | Webler | 128/692 |
| 4,721,115 | 1/1988 | Owens | 128/713 |
| 4,802,490 | 2/1989 | Johnston | 128/713 |
| 4,817,624 | 4/1989 | Newbower | 128/713 |
| 4,841,981 | 6/1989 | Tanabe | 128/692 |
| 4,869,263 | 9/1989 | Segal | 128/692 |
| 4,901,734 | 2/1990 | Griffin | 128/692 |
| 4,941,475 | 6/1990 | Williams | 128/692 |
| 4,951,682 | 8/1990 | Petre | 128/713 |

Primary Examiner—Ruth S. Smith
Assistant Examiner—Robert L. Nasser, Jr.
Attorney, Agent, or Firm—Frishauf, Holtz, Goodman & Woodward

[57] ABSTRACT

A catheter for measuring a cardiac output includes a catheter tube defining a longitudinal bore therein and having an opening near its distal end, wherein the tube bore is divided into a first lumen for installing therein a thermistor on a proximal side with respect to the opening, a second lumen in communication with the opening, and at least one third lumen. There are provided a first partition separating the first lumen and the third lumen and a second partition separating the second lumen and the third lumen, the first partition being separate from the second partition.

12 Claims, 6 Drawing Sheets

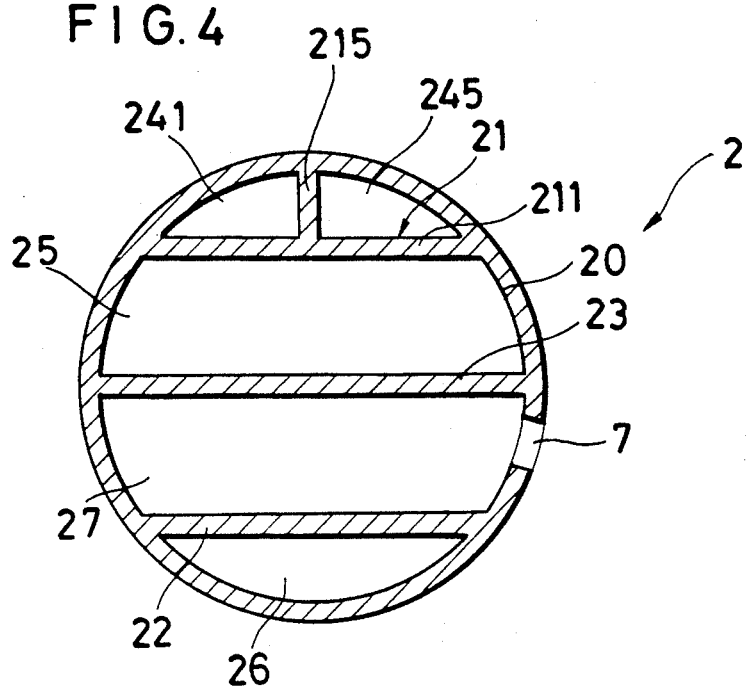
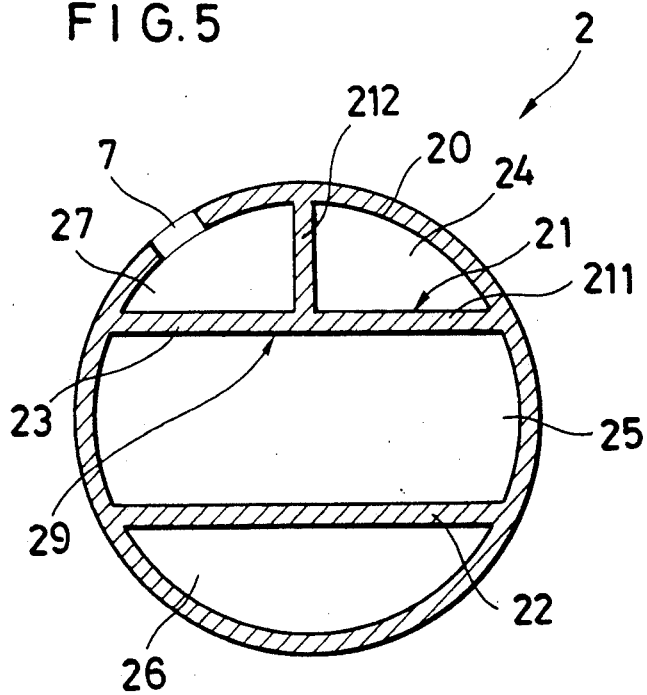

CARDIAC OUTPUT MEASURING CATHETER

This application is a continuation of application Ser. No. 07/581,469, filed Sep. 11, 1990 now abandoned.

This invention relates to a cardiac output measuring catheter adapted to be connected to a cardiac output measuring apparatus used for heart function examination.

BACKGROUND OF THE INVENTION

For heart function examination, a cardiac output is measured by a right heart catheter technique which typically relies on thermodilution. In the right heart catheter technique, the catheter is introduced from a jugular vein, femoral vein, cubital vein or the like and advanced through the superior or inferior vena cava, right atrium and right ventricle until its distal end reaches the pulmonary artery.

The catheter is provided with an injection port and a thermistor as a temperature sensing element such that the injection port is located in the right atrium and the thermistor is located in the pulmonary artery when the catheter is set in place. The injection port through which a fluid having a higher or lower temperature than the blood is introduced is located proximal of the thermistor. The temperature of the fluid as discharged is diffused and diluted in the right atrium and right ventricle. The diluted temperature is detected by the thermistor located in the pulmonary artery. A cardiac output is determined from a change with time of the detected temperature, that is, a dilution curve according to the Stewart-Hamilton method.

The cardiac output measurement by the thermodilution method is, however, intermittent and not applicable to continuous cardiac output measurement. When it is desired to take a plurality of measurements, the total amount of fluid introduced is increased, which imposes an increased burden to the patient. Repetition of such operations can increase the risk of infection.

U.S. Pat. No. 4,841,981 (or Japanese Patent Application Kokai No. 207435/1987) discloses a catheter for the continuous measurement of a cardiac output. This catheter includes temperature sensors for thermodilution measurement of a cardiac output and for measurement of a velocity of blood flow. It provides continuous measurement of blood flow velocity, from which a cardiac output is continuously calculated.

A typical arrangement of the catheter is shown in FIGS. 9 and 10. The catheter generally designated at 1 includes an elongated catheter tube 2 defining four lumens therein and having distal and proximal ends. The catheter 1 includes a pressure port 6 at the distal end of the catheter tube 2 and a balloon 8 of soft elastomer attached thereto so as to entirely surround the catheter tube over a distance of several mm from its distal end. The catheter tube 2 is provided with a side port 7 formed in the tube side wall surrounded by the balloon 8 for passage of a gas such as carbon dioxide for inflating and deflating the balloon, a second thermistor 45 spaced 10 to 20 mm apart from the distal end, a first thermistor 41 spaced 10 to 15 mm apart from the second thermistor 45 toward the proximal end, and an injection port 5 disposed proximal of the thermistors 41 and 45 and spaced 12 to 40 cm apart from the distal end.

Since this catheter is for arterial use, that is, adapted to be left in the pulmonary artery by inserting from a superior or inferior limb vein, thermistors 41 and 45 are provided on a catheter distal portion which is located downstream of the injection port 5 in the direction of blood flow. If the catheter is for venous use, that is, adapted to be left in the pulmonary vein, thermistors 41 and 45 should be provided on a catheter proximal portion which is located downstream of the injection port 5 in the blood flow direction.

The pressure port 6, balloon side port 7, thermistors 41 and 45, and injection port 5 are in communication with four independent lumens, respectively. More particularly, the pressure port 6 is in communication with a lumen 36 for measuring the external pressure such as pulmonary arterial pressure, the balloon side port 7 in communication with a balloon lumen 37, the thermistors 41 and 45 in communication with a lumen 34, and the injection port 5 in communication with a lumen 35 for injecting indicator fluid.

At the proximal end 29 of the catheter tube 2, the thermistor lumen 34 is coupled to connectors 941 and 945 through a bifurcated section of tubing such that lead wires 43 and 47 extending from the thermistors 41 and 45 are electrically connected to the connectors 941 and 945 through the thermistor lumen 34 and the section of tubing. Also, the pressure measuring lumen 36, injecting lumen 35 and balloon lumen 37 are coupled to connectors 96, 95 and 97 through sections of tubing, respectively.

The first thermistor 41 serving as a temperature sensor is for thermodilution measurement of a cardiac output whereas the second thermistor 45 is a thermistor of direct or indirect heating type which is adapted to be heated by electricity conduction or by another heater and produces a heating temperature signal representative of its own temperature, thereby sensing a blood flow velocity.

The four lumens 34, 35, 36 and 37 are defined in the interior bore of the catheter tube 2 by dividing the bore by a crisscross partition 28 into four sectors disposed about the center as shown in FIG. 10. The measuring lumen 36 is disposed adjacent the thermistor lumen 34.

On clinical application, the cardiac output measuring catheter, which is adapted for continuous measurement, is typically used in measurement for a long period of time, during which continuous fluid infusion is often needed. More particularly, it is often necessary to continuously infuse a suitable fluid through the pressure port 6 at the catheter distal end for pressure measurement. If such fluid is passed through the pressure measuring lumen 36 which is disposed adjacent the thermistor lumen 34, then the thermistors 41 and 45 are thermally affected by the fluid. In principle, the second thermistor 45 which is of the heating type is generally heated by conduction of constant current and senses its own temperature at the same time. Blood flow velocity is determined from the temperatures the first and second thermistors 41 and 45 sense and the heating current. If the temperature in the thermistor lumen 34 is substantially affected by the temperature of the fluid passing through the pressure measuring lumen 36, there occurs an inconvenience that the heating temperature signal, blood temperature signal and the value of conducting current can change, failing in accurate detection of blood flow velocity. Such thermal influence will also occur when only the first thermistor 41 for measuring a cardiac output is used.

Furthermore, the thermistor lumen 34 is disposed contiguous to the measuring lumen 36 in the above-cited publication. With the partition structure disclosed therein and illustrated in FIG. 10, even if the pressure measuring lumen is changed to lumen 37 to separate the thermistor lumen 34 from the measuring lumen (37), there still remains a risk of failing to provide accurate measurement of blood flow velocity because the partition sections are contiguous.

SUMMARY OF THE INVENTION

Therefore, an object of the present invention is to provide a novel and improved cardiac output measuring catheter which can measure both a cardiac output and a blood flow velocity while allowing infusion of a fluid, typically a transfusion fluid into the associated blood vessel through a distal end opening of the catheter without adversely affecting the cardiac output measurement.

According to the present invention, there is provided a catheter for measuring a cardiac output, comprising a catheter tube having a wall defining a longitudinal bore therein and having a distal end and a proximal end and an opening near the distal end, and partition means in the tube for dividing the bore into a first lumen for installing therein temperature sensing means, a second lumen in communication with the opening, and at least one third lumen. The partition means includes a first partition separating the first lumen and the third lumen and a second partition separating the second lumen and the third lumen, the first partition being separate from the second partition. The temperature sensing element is disposed on a proximal side with respect to the opening.

Preferably, the partition means includes a third partition for defining at least two third lumens. The third partition may extend between opposed, positions along the tube wall. It may also extend between the first and second partitions. Alternatively, it may extend between the tube wall and the first and/or second partition.

Preferably, the temperature sensing means includes a thermistor for thermodilution measurement of a cardiac output and a heating thermistor for measurement of blood flow velocity.

Preferably, the second lumen is in fluid communication with the exterior through the opening for allowing measurement of the external pressure.

Preferably, the third lumen includes a lumen having an injection port for allowing an indicator fluid for thermodilution measurement of a cardiac output to pass therethrough and exit through the injection port, the injection port being located on a proximal side with respect to the temperature sensing means.

The catheter may further include a balloon attached to the catheter tube adjacent its distal end, and the third lumen includes a lumen in fluid communication with the balloon.

In a further embodiment, the partition means includes a first partition separating the first lumen and the third lumen and a second partition separating the second lumen and the third lumen, the second partition intersecting the first partition and the tube wall.

BRIEF DESCRIPTION OF THE DRAWINGS

FIGS. 3 to 8 are enlarged transverse cross sections similar to FIG. 2 of different catheter embodiments of the invention.

DESCRIPTION OF THE PREFERRED EMBODIMENTS

Figure 9:
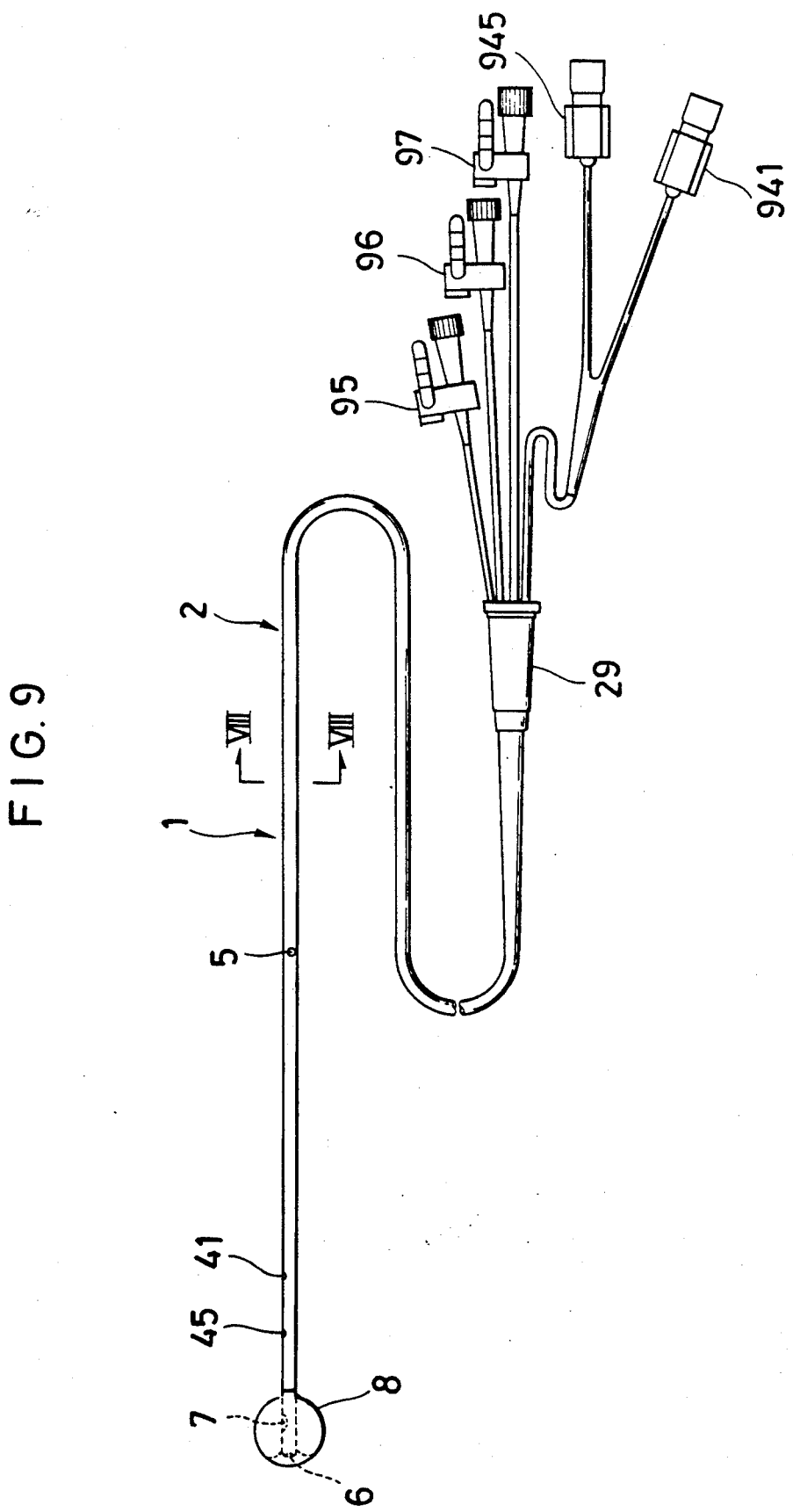
FIG. 9 is a plan view of the outline of a cardiac output measuring catheter to which the present invention is applicable.

The outline of the cardiac output measuring catheter according to the present invention is the same as the prior art cardiac output measuring catheter disclosed in Japanese Patent Application Kokai No. 207435/1987 and shown in FIG. 9. Except for the partition configuration in the catheter tube bore, the structure and function of the present catheter are identical with the prior art catheter. If desired, the cardiac output measuring catheter of the present invention may be of the construction having only the first thermistor 41 installed in the thermistor lumen for measuring a cardiac output.

Basically, the cardiac output measuring catheter of the present invention includes an elongated catheter tube having a distal end and a proximal end and defining at least three (first, second and third) longitudinally extending lumens extending therethrough. The catheter includes at least one temperature sensing element typically in the form of a thermistor.

The first lumen comprises at least one lumen which is assigned as a thermistor lumen, that is, a lumen having a thermistor installed therein. Usually, a single lumen is commonly used for the first and second thermistors 41 and 45 with their lead wires although a plurality of thermistors may be independently accommodated in separate lumens.

The second lumen comprises at least one lumen having an opening or port located closer to the distal end than is the thermistor installed in the first lumen. The second lumen is typically a lumen having a pressure port for measuring the external pressure, typically the pressure of a pulmonary artery when the catheter is intended for use with its distal end left in the pulmonary artery. Another lumen having a port for infusing a fluid may be additionally provided. In the case of a catheter whose distal end is to be left in the pulmonary vein in which a lumen for injecting an indicator fluid has an injection port located distal of the thermistor, the second lumen includes this indicator fluid injecting lumen in addition to the pressure measuring lumen.

The third lumen defined in the catheter tube should have no or negligible thermal influence on the thermistor(s) and is typically a lumen for injecting an indicator fluid in the case of a catheter whose distal end is to be left in the pulmonary artery. Since an injection port is located proximal of the thermistor in this case, the portion of the indicator injecting lumen that extends from the injection port toward the distal end is blocked with a resin filling at a position proximal of the thermistor(s) to prevent the fluid from reaching the thermistor installed site, thereby eliminating any thermal influence of the indicator fluid on the thermistor(s) as well as any thermal influence of the self-heating thermistor on the indicator fluid.

If the indicator injecting lumen is not blocked and the fluid is thus permitted to flow through the indicator injecting lumen to the distal portion where the thermistor is installed, then this lumen is considered to belong to the second lumen.

The catheter of the invention need not necessarily have a balloon. Provision of a balloon lumen is preferable because a fluid to be introduced into the balloon there through, typically a gas such as carbon dioxide has a thermal insulation function, reducing thermal influence. Also included in the third lumen is a lumen for infusing a medicament fluid.

Three or more, typically four or five lumens as mentioned above are defined in the catheter by providing suitable partition means for dividing or separating the bores in a transverse cross section.

Figure 1:
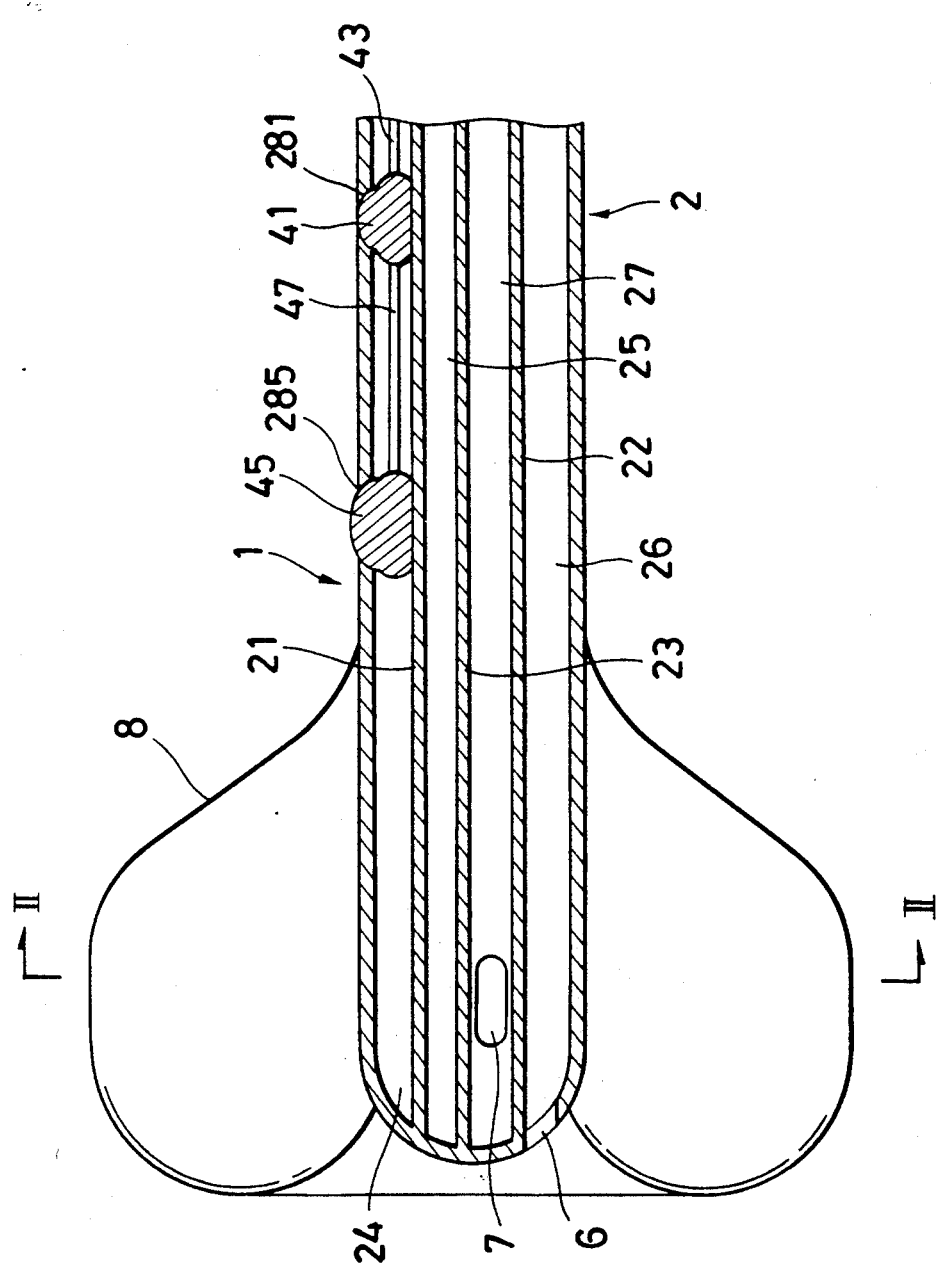
FIG. 1 is an axial cross section of a distal portion of a cardiac output measuring catheter according to one embodiment of the invention.
Figure 2:
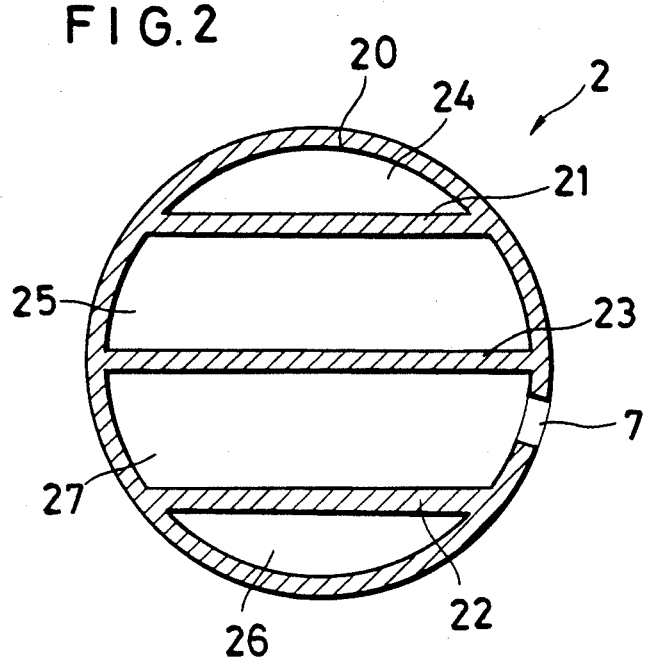
FIG. 2 is an enlarged transverse cross section of the catheter taken along lines II—II in FIG. 1.

Referring to FIGS. 1 and 2, there is illustrated a distal portion of a catheter according to one embodiment of the invention. The catheter 1 has a catheter tube 2 defining a longitudinally extending bore therein. The tube is provided with partition means including a first partition 21 for defining a thermistor lumen 24 as the first lumen with an arcuate portion of the tube wall 20 and a second partition 22 for defining a pressure measuring lumen 26 as the second lumen with another arcuate portion of the tube wall 20. The first and second partitions 21 and 22 are separate or independent from each other. Differently stated, the first partition 21 does not intersect the second partition 22.

More particularly, the bore of the catheter tube 2 is partitioned into four sections by three longitudinally extending, generally parallel, transversely spaced apart plate-shaped partitions 21, 22 and 23 each extending chordally between opposed positions along the tube wall 20 as shown in FIGS. 1 and 2.

The first partition 21 and an arcuate portion of the tube wall 20 define the thermistor lumen 24 as the first lumen near the bore periphery. The thermistor lumen 24 includes side ports 281 and 285 formed throughout the tube wall 20 and having first and second thermistors 41 and 45 mounted therein, respectively. Lead wires 43 and 47 from the thermistors 41 and 45 extend through the thermistor lumen 24 toward the proximal end. It is to be understood that the first thermistor 41 is a thermistor for thermodilution measurement of a cardiac output and the second thermistor 45 is a thermistor of direct or indirect heating type, preferably self-heating type for measuring a blood flow velocity, respectively, as previously described. For the construction and function of these thermistors, reference should be made to Japanese Patent Application Kokai No. 207435/1987.

The second partition 22 which is approximately parallel and diametrically opposite to the first partition 21 is formed in the bore. The second partition 22 and an arcuate portion of the tube wall 20 define the pressure measuring lumen 26 as the second lumen near the bore periphery. The pressure measuring lumen 26 is in communication with a pressure port in the form of an opening 6 in the distal end wall of the tube 2 so that the external pressure can be measured by way of this lumen 26. Alternatively, a transfusion fluid may be continuously administered through this lumen 26.

The central partition 23 defines an indicator fluid injecting lumen 25 and a balloon lumen 27 with the first and second partitions 21 and 22, respectively. The balloon lumen 27 is in communication with a port 7 in the tube side wall and allows for passage of a gas to and from the balloon 8 for inflation and deflation. The indicator fluid injecting lumen 25 is in communication with the injection port 5 is shown in FIG. 9 which shows the general configuration which is common to both the prior art and the present invention. It is to be noted that the portion of the indicator fluid injecting lumen 25 which extends from the injection port 5 toward the distal end is blocked with a resin plug such as polyvinyl chloride through not shown in the figures. A fluid for cardiac output measurement is discharged through the port 5 and does not internally flow in proximity to the thermistors 41 and 45.

Since the first and second partitions 21 and 22 for defining the thermistor lumen 24 as the first lumen and the pressure measuring lumen 26 as the second lumen are provided separate, any fluid, especially a transfusion fluid introduced into the pressure measuring lumen 26 gives no or little thermal influence on the thermistors 41 and 45, eliminating any disturbance on the measurement of a blood flow velocity.

In the illustrated embodiment, the balloon lumen 27 between the thermistor lumen 24 and the pressure measuring lumen 26 receives a gas for inflation and deflation and a distal portion of the indicator fluid injecting lumen 25 which is blocked with a plug for preventing further entry of the indicator fluid is filled with air or suitable gas. Thermal insulation of these filling gases enhances the benefits of the invention.

Since the thermistors 41, 45 and the injection port 5 are preferably located at a relatively circumferentially close distance on the tube periphery, the indicator fluid injecting lumen 25 is preferably disposed contiguous to the thermistor lumen 24.

If it is desired to introduce a fluid to a distal portion of the indicator fluid injecting lumen 25 or if a catheter is intended for use with its distal end left in the pulmonary vein, the indicator fluid injecting lumen 25 and the balloon catheter 27 are reversed from the illustrated arrangement. Then the partition 23 functions as a second partition with the benefits of the invention because the partitions 21 and 23 are separate from each other.

In a typical example, the catheter tube 2 has an inner diameter of about 0.8 to about 2.5 mm. The first and second partitions are generally spaced a distance of about 0.4 to about 1.5 mm.

Figure 3:
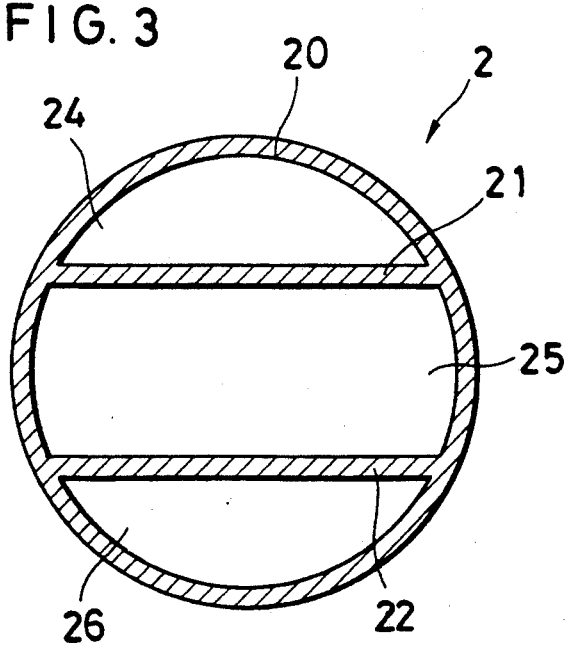

Turning now to FIGS. 3 and 4, there are illustrated further embodiments which are modifications of the embodiment of FIGS. 1 and 2.

The embodiment of FIG. 3 is of the three lumen structure obtained by omitting the central partition from the embodiment of FIGS. 1 and 2. Differently stated, the balloon lumen 27 is omitted from the FIG. 2 embodiment while the balloon 8 and side port 7 are omitted too. The partition means includes only the first and second spaced apart partitions 21 and 22 which chordally extend between opposed positions along the tube wall 20 and do not intersect with each other whereby the thermistor lumen 24 and the pressure measuring lumen 26 are separated by the indicator fluid injecting lumen 25.

The embodiment of FIG. 4 is of the five lumen structure obtained by adding a partition segment to the first partition 21 of the FIG. 2 embodiment to divide the thermistor lumen 24 into two thermistor lumens 241 and 245. More particularly, a chordal partition 211 similar to the first partition 21 of the FIG. 2 embodiment is provided and another partition 215 is extended between the tube wall 20 and the partition 211. The other partition 215 defines with the partition 211 sections and the tube wall two thermistor lumens 241 and 245 for receiving thermistors 41 and 45, respectively.

In the FIG. 4 embodiment, both the separated thermistor lumens 241 and 245 belong to the first lumen. The partitions 211 and 215 defining these lumens 241 and 245 with arcuate portions of the tube wall 20 function as the first partition. Both the partitions 211 and 215 are separate from the second partition 22.

FIG. 5 shows a still other embodiment in which two partitions 22 and 29 extend generally parallel to each other and chordally between opposed positions along the tube wall 20. A partition segment 212 extends between the tube wall 20 and the partition 29. A segment 211 of partition 29, partition 212 and a tube wall arcuate portion define a thermistor lumen 24; a segment 23 of partition 29, partition segment 212 and a tube wall arcuate portion define a balloon lumen 27; partitions 29 and 22 and opposed tube wall arcuate portions define an indicator fluid injecting lumen 25; partition 22 and a tube wall arcuate portion define a pressure measuring lumen 26.

In this embodiment, the partition segments 211 and 212 defining the thermistor lumen 24 as the first lumen form the first partition 21, which is separate from the second partition 22 defining the pressure measuring lumen 26 as the second lumen.

It is to be understood that, as seen in FIG. 5, the indicator fluid injecting lumen 25 and the balloon lumen 27 are defined between the thermistor lumen 24 (first lumen) and the pressure measuring lumen 26 (second lumen). Namely, the two lumens 25 and 27 are separated by the third partition 23.

In this embodiment, the third partition 23 is connected to the segment 211 of the first partition to form the straight partition 29. Differently stated, the third partition 23 interconnects the tube wall 20 and the first partition 21.

In the design that the first and second partitions 21 and 22 are provided in the tube bore such that they do not interconnect or intersect, a plurality of third lumens can be defined by providing the third partition 23 which is not interconnected or intersected with the first and second partitions 21 and 22 as shown in FIGS. 2 and 4 or by providing the third partition 23 which is interconnected to the first partition 21 and the tube wall 20 as shown in FIG. 5. The benefits of the invention are obtained in either case.

The balloon lumen 27 and the indicator fluid injecting lumen 25 as the third lumen produce a heat insulating function. In such a case, the third partition 23 can interconnect the tube wall 20 and the second partition 22. Alternatively, the third partition 23 can interconnect the first and second partitions 21 and 22. The third partition 23 may comprise a plurality of segments.

Therefore, according to a further aspect of the invention, first and second separate partitions define first and second lumens within the bore of a catheter tube with arcuate portions of the tube wall. At least one third partition is extended between a selected position on the first and second partitions and the tube wall to define at least two third lumens between the first and second partitions.

Figure 6:
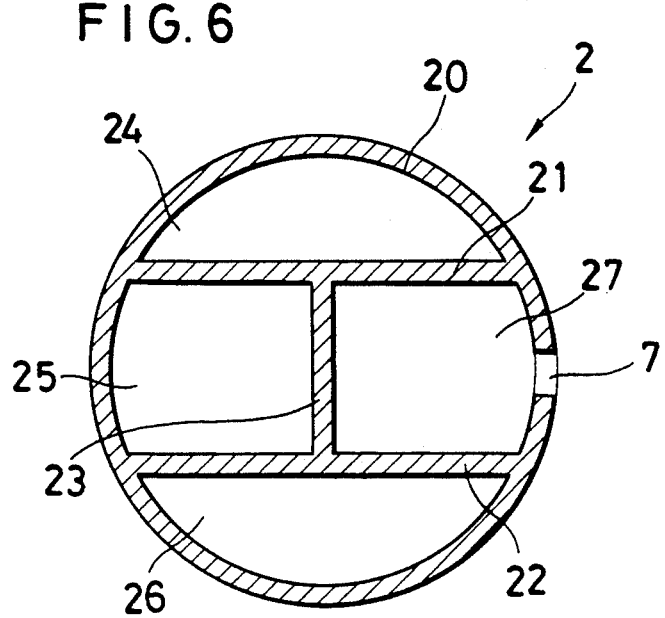

FIG. 6 illustrates one such embodiment in which a catheter is intended to be left in the pulmonary artery. As in FIG. 3, the catheter tube 2 is provided with longitudinally extending, parallel, transversely spaced apart first and second partitions 21 and 22 in the bore to define a first or thermistor lumen 24 and a second or pressure measuring lumen 26. A third partition 23 bridges between the first and second partitions 21 and 22. The third partition 23 intersects the first and second partitions 21 and 22 at right angles and at the center in the figure though not limited thereto. The third partition 23 thus divides the space between the first and second partitions 21 and 22 into a balloon lumen 27 and an indicator fluid injecting lumen 25 (entry of fluid to its distal portion is prevented by a plug as in the previous embodiment), both belonging to the third lumen.

Figure 7:
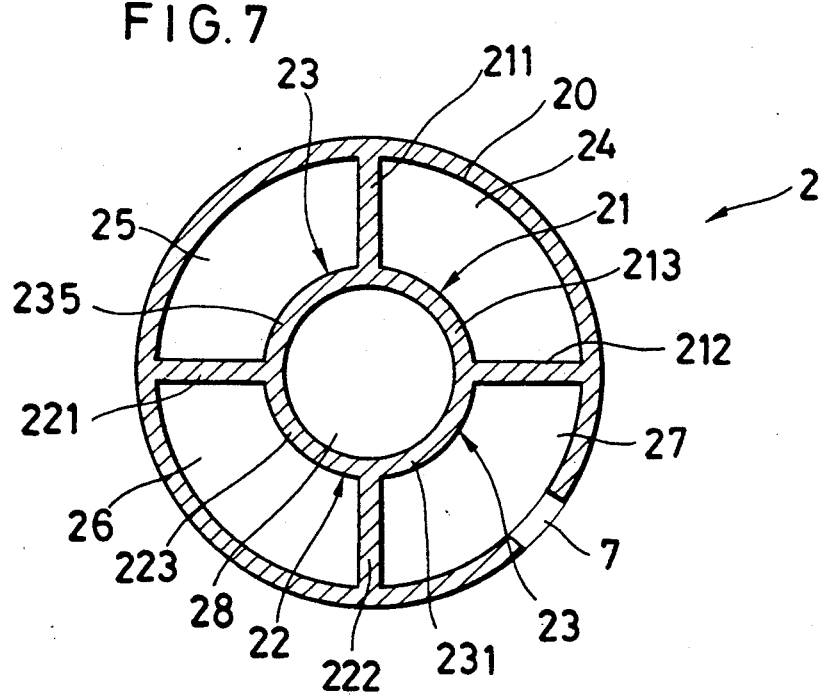

FIG. 7 illustrates another embodiment. The partition means is comprised of a concentric annular section and radial sections radially extending from the annular section to the tube wall. More particularly, a first partition 21 consisting of radial segments 211, 212 and an arcuate segment 213 defines a sector-shaped first or thermistor lumen 24. A second partition 22 consisting of radial segments 221, 222 and an arcuate segment 223 defines a sector-shaped second or pressure measuring lumen 24. The first and second partitions 21 (211, 212, 213) and 22 (221, 222, 223) are connected by arcuate segments 231 and 235 to define three third lumens 25, 27 and 28. Among these, the coaxial sector lumens 25 and 27 disposed along the outer periphery of the bore are an indicator fluid injecting lumen and a balloon lumen, respectively. The central circular lumen 28 is normally filled with air or a suitable gas for thermal insulation. While the central lumen 28 is typically filled with air or another suitable gas, it may also serve as a self-sustaining means for receiving a guide wire therein for facilitating insertion of the catheter into the body.

It is understood that the third partition segments 231 and 235 interconnect the first and second partitions 21 and 22 in the FIG. 7 embodiment.

Figure 8:
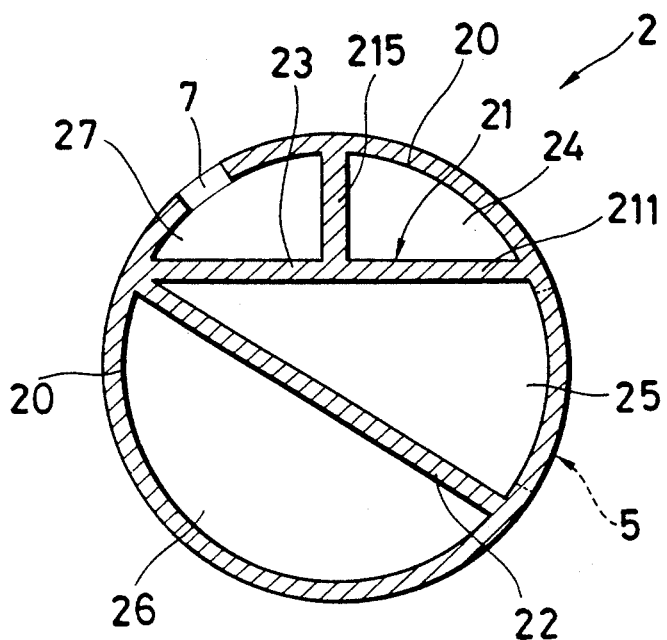
Figure 10:
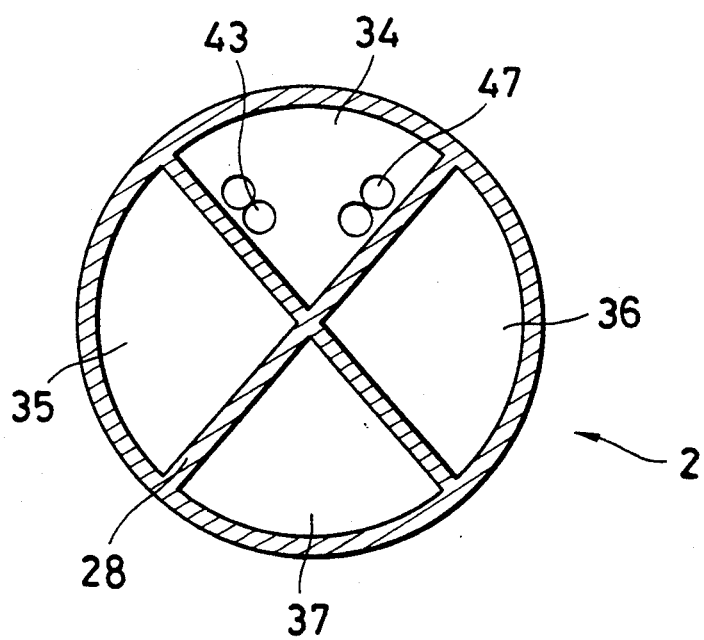
FIG. 10 is an enlarged transverse cross section of the catheter taken along lines X—X in FIG. 9, but of a prior art catheter.

FIG. 8 shows a still further embodiment which is a modified version of the FIG. 5 embodiment. The FIG. 8 embodiment is obtained by rotating clockwise the second partition 22 from the position shown in FIG. 5, that is, by moving the connection between the second partition 22 and the tube wall 20 from the position shown in FIG. 5 to the connection between the third partition 23 and the tube wall 20. As a result, the second partition 22 and the first partition segment 211 connected to the third partition 23 form a V shape. Where the indicator fluid injecting lumen 25 opens through the injection port 5, a larger opening is available without reducing the cross-sectional area of the pressure measuring lumen 26, thus offering a reduced resistance against the indicator fluid to be injected and ease of formation of such an opening. The benefits of the invention are also achieved in this embodiment since the first partition 21 consisting of partition segments 211 and 215 is separated from the second partition 22 by the third partition 23.

The material and dimensions of the catheter tube and partitions are not critical to the invention. The catheter tube may be formed of any suitable resin such as polyurethane, polyvinyl chloride, ethylene-vinyl acetate copolymers, polyethylene, and polypropylene. The partitions are preferably formed integral with the tube. The balloon may be formed of latex rubber or silicone rubber. In general, the catheter tube has a wall thickness of about 0.1 to about 0.5 mm and the partitions 21, 22, 23, etc. have a thickness of about 0.05 to 0.5 mm.

Preferably, at least the portion of the catheter tube which is to be left in the blood vessel is coated on the outer surface with an anti thrombus agent. Such a coating can prevent thrombus formation during continuous cardiac output measurement for a long time. Hydroxyethyl methacrylate and styrene copolymers are preferred anti thrombus agents.

The construction and operation of the cardiac output measuring catheter other than the partition means forming the present invention are described in Japanese Patent Application Kokai No. 207435/1987.

The cardiac output measuring catheter of the invention enables measurement of a cardiac output while allowing a transfusion fluid to be introduced through a pressure port for pressure measurement at the same time.

Although some preferred embodiments have been described, many modifications and variations may be made thereto in the light of the above teachings. It is therefore to be understood that within the scope of the appended claims, the invention may be practiced otherwise than as specifically described.

We claim:

1. A catheter for measuring a cardiac output, comprising:
    a catheter tube having a wall defining a longitudinal bore therein, said catheter tube having a distal end and a proximal end, and an opening near the distal end,
    partition means in said catheter tube for dividing said bore into a first lumen, a second lumen in fluid communication with said opening near the distal end of said catheter tube, and at least one third lumen interposed between said first and second lumens and completely separating said first lumen from said second lumen,
    a distal portion of said at least one third lumen being filled with gas means for providing thermal insulation, and
    temperature sensing means mounted in said first lumen, said temperature sensing means including a temperature sensing element and lead wires connected to said temperature sensing element, said lead wires extending through at least a portion of said first lumen,
    said partition means including:
        a first partition separating said first lumen and said at least one third lumen, and
        a second partition separating said second lumen and said at least one third lumen,
        said first partition being separated from said second partition, and
    said temperature sensing element is disposed on a proximal side of said catheter tube with respect to said opening in said bore of said catheter tube.

2. The catheter of claim 1 wherein said partition means includes a third partition arranged between said first and second partitions, for defining at least two third lumens interposed between said first and second lumens.

3. The catheter of claim 2 wherein said third partition extends between opposed positions along said wall of said catheter tube.

4. The catheter of claim 2 wherein said third partition extends between said first and second partitions and is connected to said first and second partitions.

5. The catheter of claim 2 wherein said third partition extends between said wall of said catheter tube and one of said first and second partitions.

6. The catheter of claim 2 wherein said third partition extends between said wall of said catheter tube and said first and second partitions.

7. The catheter of claim 1 wherein said temperature sensing element includes a thermistor for thermodilution measurement of a cardiac output, and a heating thermistor for measurement of blood flow velocity.

8. The catheter of claim 1 wherein said second lumen is in fluid communication with the exterior of said catheter tube through said opening for allowing measurement of an external pressure.

9. The catheter of claim 1 wherein said at least one third lumen includes a lumen having an injection port for allowing an indicator fluid for thermodilution measurement of a cardiac output to pass therethrough and to exit through said injection port, said injection port being located on a proximal side of said catheter tube with respect to said temperature sensing element.

10. The catheter of claim 1, further comprising a balloon attached to said catheter tube adjacent its distal end, and wherein said at least one third lumen includes a lumen in fluid communication with the interior of said balloon.

11. A catheter for measuring a cardiac output, comprising:
    a catheter tube having a distal end,
    a first lumen in said catheter tube,
    a temperature sensing element and associated lead wires received in said first lumen,
    a second lumen in said catheter tube and opening at said distal end of said catheter tube,
    a third lumen in said catheter tube and interposed between said first and second lumens to completely separate said first and second lumens from each other and to provide heat insulation between said first and second lumens, and
    a further lumen interposed between said first and second lumens, said further lumen being filled at a distal end portion thereof with gas means for providing thermal insulation between said first and second lumens.

12. The catheter of claim 11, further comprising a balloon attached to said catheter tube adjacent its distal end, and wherein said third lumen includes a lumen portion in fluid communication with the interior of said balloon.

* * * * *